(12) United States Patent
Zhao et al.

(10) Patent No.: US 12,727,933 B2
(45) Date of Patent: Sep. 8, 2026

(54) ELECTROSURGICAL INSTRUMENTS AND SYSTEMS INCLUDING THERMAL CUTTING ELEMENTS

(71) Applicant: Covidien LP, Mansfield, MA (US)

(72) Inventors: Yanzhu Zhao, Blaine, MN (US); Daniel A. Joseph, Golden, CO (US)

(73) Assignee: Covidien LP, Mansfield, MA (US)

( * ) Notice: Subject to any disclaimer, the term of this patent is extended or adjusted under 35 U.S.C. 154(b) by 842 days.

(21) Appl. No.: 16/785,330

(22) Filed: Feb. 7, 2020

(65) Prior Publication Data

US 2021/0244464 A1 Aug. 12, 2021

(51) Int. Cl.
*A61B 18/14* (2006.01)
*A61B 18/00* (2006.01)

(52) U.S. Cl.
CPC ............................... *A61B 18/1445* (2013.01); *A61B 2018/00077* (2013.01); *A61B 2018/00601* (2013.01); *A61B 2018/00714* (2013.01)

(58) Field of Classification Search
CPC ............ A61B 18/1445; A61B 18/1442; A61B 18/085; A61B 18/14; A61B 18/12; A61B 18/04; A61B 2018/00077; A61B 2018/00714; A61B 2018/00601; A61B 2018/00607; A61B 2018/1452; A61B 2018/00994; A61B 2018/144; A61B 2018/1405; A61B 2018/00654; A61B 2018/00178; A61B 2018/146; A61B 2018/1422; A61B 2018/1412; A61B 2018/1407; A61B 2018/141; A61B 2018/00107; A61B 2018/00101; A61B 2018/00095; A61B 2018/00148; A61B 2018/00005; A61B 2017/00039; A61B 2017/00876; A61B 5/062; H05K 1/0242; H01F 38/14; H01F 27/2823
See application file for complete search history.

(56) References Cited

U.S. PATENT DOCUMENTS 2,068,721 A 1/1937 Wappler
4,091,813 A 5/1978 Shaw et al.
(Continued)

OTHER PUBLICATIONS https://www.microwaves101.com/encyclopedias/surface-roughness (Year: 2016).*

*Primary Examiner* — Joseph A Stoklosa
*Assistant Examiner* — Marina Delaney Templeton

(57) ABSTRACT

An electrosurgical instrument includes an end effector assembly including first and second jaw members. At least one of the first or second jaw members is movable relative to the other from a spaced-apart position to an approximated position to grasp tissue therebetween. A thermal cutting wire is disposed on at least a portion of at least one of the first or second jaw members. The thermal cutting wire is configured for ferromagnetic heating to provide automatic Curie temperature control upon supply of an AC signal thereto. The thermal cutting wire may include a conductive core, an inner ferromagnetic coating disposed about the conductive core, and an outer ferromagnetic coating disposed about the inner ferromagnetic coating. The thermal cutting wire may alternatively or additionally include an exposed outer surface defining a roughness configured to facilitate attenuation during ferromagnetic heating.

13 Claims, 11 Drawing Sheets

(56) References Cited

U.S. PATENT DOCUMENTS 4,219,025 A * 8/1980 Johnson ............... A61B 18/082 219/241
5,389,098 A 2/1995 Tsuruta et al.
5,403,312 A 4/1995 Yates et al.
5,465,895 A 11/1995 Knodel et al.
5,810,811 A 9/1998 Yates et al.
5,827,271 A 10/1998 Buysse et al.
5,833,690 A 11/1998 Yates et al.
5,876,401 A 3/1999 Schulze et al.
5,911,719 A 6/1999 Eggers
6,024,741 A 2/2000 Williamson, IV et al.
6,086,586 A 7/2000 Hooven
6,273,887 B1 8/2001 Yamauchi et al.
6,402,747 B1 6/2002 Lindemann et al.
6,602,252 B2 8/2003 Mollenauer
6,736,813 B2 5/2004 Yamauchi et al.
6,776,780 B2 8/2004 Mulier et al.
6,802,843 B2 10/2004 Truckai et al.
6,808,525 B2 10/2004 Atterell et al.
6,821,273 B2 11/2004 Mollenauer
6,860,880 B2 3/2005 Treat et al.
6,899,710 B2 5/2005 Hooven
6,929,641 B2 8/2005 Goble et al.
6,953,461 B2 10/2005 McClurken et al.
7,011,656 B2 3/2006 McGaffigan et al.
7,033,356 B2 4/2006 Latterell et al.
7,070,597 B2 7/2006 Truckai et al.
7,083,619 B2 8/2006 Truckai et al.
7,112,201 B2 9/2006 Truckai et al.
7,125,409 B2 10/2006 Truckai et al.
7,147,637 B2 12/2006 Goble
7,169,146 B2 1/2007 Truckai et al.
7,204,835 B2 4/2007 Latterell et al.
7,270,664 B2 9/2007 Johnson et al.
7,276,068 B2 10/2007 Johnson et al.
7,326,202 B2 2/2008 McGaffigan
7,329,255 B2 2/2008 McGaffigan
7,354,440 B2 4/2008 Truckal et al.
7,357,802 B2 4/2008 Palanker et al.
7,364,577 B2 4/2008 Wham et al.
7,396,356 B2 7/2008 Mollenauer
7,419,490 B2 9/2008 Falkenstein et al.
7,686,827 B2 3/2010 Hushka
7,815,641 B2 10/2010 Dodde et al.
7,931,649 B2 4/2011 Couture et al.
8,034,051 B2 10/2011 Martin et al.
8,162,940 B2 4/2012 Johnson et al.
8,187,273 B2 5/2012 Kerr et al.
8,197,472 B2 6/2012 Lau et al.
8,226,649 B2 7/2012 Falkenstein et al.
8,292,879 B2 10/2012 Manwaring et al.
8,303,585 B2 11/2012 Mollenauer
8,372,066 B2 2/2013 Manwaring et al.
8,377,052 B2 2/2013 Manwaring et al.
8,394,094 B2 3/2013 Edwards et al.
8,425,503 B2 4/2013 Manwaring et al.
8,491,578 B2 7/2013 Manwaring et al.
8,491,626 B2 7/2013 Roy et al.
8,523,850 B2 9/2013 Manwaring et al.
8,523,852 B2 9/2013 Manwaring et al.
8,551,088 B2 10/2013 Falkenstein et al.
8,562,598 B2 10/2013 Falkenstein et al.
8,568,411 B2 10/2013 Falkenstein et al.
8,597,293 B2 12/2013 Falkenstein et al.
8,597,297 B2 12/2013 Couture et al.
8,617,151 B2 12/2013 Denis et al.
8,623,003 B2 1/2014 Lau et al.
8,636,730 B2 1/2014 Keppel
8,734,445 B2 5/2014 Johnson et al.
8,915,909 B2 12/2014 Manwaring et al.
8,932,279 B2 1/2015 Stringham et al.
8,951,248 B2 2/2015 Messerly et al.
9,005,199 B2 4/2015 Beckman et al.
9,039,694 B2 5/2015 Ross et al.
9,050,100 B2 6/2015 Yates et al.
9,084,606 B2 7/2015 Greep
9,131,977 B2 9/2015 Manwaring et al.
9,149,321 B2 10/2015 Stringham et al.
9,192,427 B2 11/2015 Johnson et al.
9,265,553 B2 2/2016 Manwaring et al.
9,265,554 B2 2/2016 Manwaring et al.
9,265,555 B2 2/2016 Manwaring et al.
9,265,556 B2 2/2016 Manwaring et al.
9,320,560 B2 4/2016 Manwaring et al.
9,387,037 B2 7/2016 Yang
9,402,679 B2 8/2016 Ginnebaugh et al.
9,579,146 B2 2/2017 Johnson et al.
9,918,774 B2 3/2018 Batchelor et al.
9,931,157 B2 4/2018 Strobl et al.
9,955,858 B2 5/2018 Pamnani et al.
10,085,794 B2 10/2018 Kerr et al.
10,204,773 B2 2/2019 Sugiyama et al.
10,213,247 B2 2/2019 Manwaring et al.
2001/0010272 A1* 8/2001 Otsuka ................. H05K 1/0242 174/258
2004/0006340 A1* 1/2004 Latterell ............ A61B 18/1442 606/48
2007/0078452 A1* 4/2007 Sekino ................... A61B 17/29 606/27
2007/0265616 A1 11/2007 Couture et al.
2010/0274244 A1* 10/2010 Heard ................ A61B 18/1442 606/45
2013/0012934 A1* 1/2013 Manwaring ............ A61B 18/10 606/29
2013/0218152 A1* 8/2013 Manwaring ........ A61B 18/1492 606/30
2014/0135804 A1 5/2014 Weisenburgh, II et al.
2015/0088128 A1* 3/2015 Couture ............. A61B 18/1445 606/42
2016/0249975 A1* 9/2016 Konishi ............. A61B 18/1445 606/45
2017/0156788 A1 6/2017 Johnson et al.
2017/0196648 A1 7/2017 Ward et al.
2018/0147405 A1* 5/2018 McCabe ........... H01J 37/32009
2018/0303322 A1 10/2018 Pamnani et al.
2019/0000538 A1 1/2019 Widenhouse et al.
2020/0237423 A1* 7/2020 Witte ................. A61G 13/1245

* cited by examiner

ELECTROSURGICAL INSTRUMENTS AND SYSTEMS INCLUDING THERMAL CUTTING ELEMENTS

FIELD

The present disclosure relates to electrosurgical instruments and systems and, more particularly, to electrosurgical instruments such as electrosurgical forceps (and systems including the same) incorporating thermal cutting elements to facilitate tissue treatment and/or cutting tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is an electrosurgical instrument including an end effector assembly having first and second jaw members. At least one of the first or second jaw members is movable relative to the other from a spaced-apart position to an approximated position to grasp tissue between first and second opposed surfaces of the first and second jaw members, respectively. The first jaw member includes a thermal cutting wire including a first portion extending distally along at least a portion of a length of the first opposed surface and a second portion extending about a distal tip of the first jaw member. The first and second portions of the thermal cutting wire each include a ferromagnetic coating such that the first and second portions are ferromagnetically heated and provide automatic Curie temperature control upon supply of an AC signal thereto.

In an aspect of the present disclosure, the first portion defines a first Curie temperature and the second portion defines a second Curie temperature different from the first Curie temperature. Alternatively, the Curie temperatures of the first and second portions may be the same.

In another aspect of the present disclosure, the ferromagnetic coating of the first portion is different from the ferromagnetic coating of the second portion, e.g., different in thickness, surface roughness, and/or material. Alternatively, the coatings may be the same.

In yet another aspect of the present disclosure, the first and the second portions are independently activatable.

In still another aspect of the present disclosure, the second portion extends from the first portion and a third portion extends from the second portion proximally at least one of through the first jaw member or along an outer exterior surface of the first jaw member. IN such aspects, a branch wire may branch off from the thermal cutting wire between the first portion and the second portion and extend proximally at least one of through the first jaw member or along an outer exterior surface of the first jaw member to enable independent activation of the first and second portions.

In still yet another aspect of the present disclosure, the first jaw member includes an electrically-conductive plate defining at least a portion of the first opposed surface.

In another aspect of the present disclosure, the first portion of the thermal cutting wire extends at least partially within a depression defined within the electrically-conductive plate.

In another aspect of the present disclosure, the first portion of the thermal cutting wire extends at least partially within a channel defined between spaced-apart portions of the electrically-conductive plate.

Another electrosurgical instrument provided in accordance with the present disclosure includes an end effector assembly having first and second jaw members. At least one of the first or second jaw members is movable relative to the other from a spaced-apart position to an approximated position. The first jaw member includes a first jaw housing supporting a first electrically-conductive plate thereon that defines a first longitudinally-extending channel. An elastomer is disposed at least partially within the first longitudinally-extending channel. The second jaw member includes a second jaw housing supporting a second electrically-conductive plate thereon that defines a second longitudinally-extending channel. A thermal cutting wire is disposed at least partially within the second longitudinally-extending channel and positioned to oppose the elastomer in the approximated position of the end effector assembly. The thermal cutting wire includes a ferromagnetic coating such that the thermal cutting wire is ferromagnetically heated and provides automatic Curie temperature control upon supply of an AC signal thereto.

In an aspect of the present disclosure, the thermal cutting wire includes first and second segments extending in side-by-side relation relative to one another at least partially within the second longitudinally-extending channel. In such aspects, the first and second segments may be joined at distal ends thereof.

In another aspect of the present disclosure, the thermal cutting wire includes a conductive core. In such aspects, the ferromagnetic coating is disposed about the conductive core.

In still another aspect of the present disclosure, the thermal cutting wire defines a Curie temperature of between 400° C. and 600° C. Other temperature or temperature ranges are also contemplated.

Another electrosurgical instrument provided in accordance with aspects of the present disclosure includes an end effector assembly having first and second jaw members. At least one of the first or second jaw members is movable relative to the other from a spaced-apart position to an approximated position. The first jaw member includes a jaw housing supporting an electrically-conductive plate thereon and a thermal cutting wire disposed on and extending at least partially along a length of the electrically-conductive plate. The thermal cutting wire includes a conductive core, a ferromagnetic coating disposed about the conductive core, and a thermally-conductive, electrically-insulative material that electrically isolates the thermal cutting wire from the electrically-conductive plate. The ferromagnetic coating enables the thermal cutting wire to be ferromagnetically heated and provide automatic Curie temperature control upon supply of an AC signal thereto.

In an aspect of the present disclosure, the thermally-conductive, electrically-insulative material is ceramic.

In another aspect of the present disclosure, the thermally-conductive, electrically-insulative material is coated about the ferromagnetic coating. Alternatively or additionally, the thermally-conductive, electrically-insulative material is disposed between the ferromagnetic coating and the electrically-conductive plate.

In yet another aspect of the present disclosure, the thermal cutting wire is at least partially disposed within a longitudinally-extending depression defined within the electrically-conductive plate.

Another electrosurgical instrument provided in accordance with the present disclosure includes an end effector assembly having first and second jaw members at least one of which is movable relative to the other from a spaced-apart position to an approximated position to grasp tissue therebetween. A thermal cutting wire is disposed on at least a portion of at least one of the first or second jaw members and includes a conductive core, an inner ferromagnetic coating disposed about the conductive core, and an outer ferromagnetic coating disposed about the inner ferromagnetic coating. The thermal cutting wire is configured for ferromagnetic heating to provide automatic Curie temperature control upon supply of an AC signal thereto.

In an aspect of the present disclosure, the inner ferromagnetic coating defines a first thickness and the outer ferromagnetic coating defines a second, different thickness. In aspects, the first thickness is greater than the second thickness.

In another aspect of the present disclosure, the inner ferromagnetic coating is formed from a first material and the outer ferromagnetic coating is formed from a second, different material. The second material may define a relatively greater permeability compared to the first material and/or the first material may define a relatively greater magnetic loss compared to the second material.

In still another aspect of the present disclosure, the inner ferromagnetic coating defines a first Curie temperature and the outer ferromagnetic coating defines a second Curie temperature different from the first Curie temperature. In such aspects, the second Curie temperature may be greater than the first Curie temperature.

In yet another aspect of the present disclosure, a portion of the thermal cutting wire extends along a tissue-treating surface of one of the first or second jaw members. Additionally or alternatively, a portion of the thermal cutting wire extends about a distal tip of one of the first or second jaw members.

Another electrosurgical instrument provided in accordance with the present disclosure includes an end effector assembly having first and second jaw members at least one of which is movable relative to the other from a spaced-apart position to an approximated position to grasp tissue therebetween. A thermal cutting wire is disposed on at least a portion of at least one of the first or second jaw members. The thermal cutting wire includes a ferromagnetic coating configured for ferromagnetic heating to provide automatic Curie temperature control upon supply of an AC signal thereto. The ferromagnetic coating defines an exposed outer surface and the exposed outer surface defines a roughness configured to facilitate attenuation during ferromagnetic heating.

In an aspect of the present disclosure, the roughness is patterned. Alternatively, the roughness may be random.

In another aspect of the present disclosure, the roughness is correlated with a skin depth of the thermal cutting wire. More specifically, in aspects, a ratio of the roughness to the skin depth is between 2:1 and 3:1.

In yet another aspect of the present disclosure, a portion of the thermal cutting wire extends along a tissue-treating surface of one of the first or second jaw members. Additionally or alternatively, a portion of the thermal cutting wire extends about a distal tip of one of the first or second jaw members.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
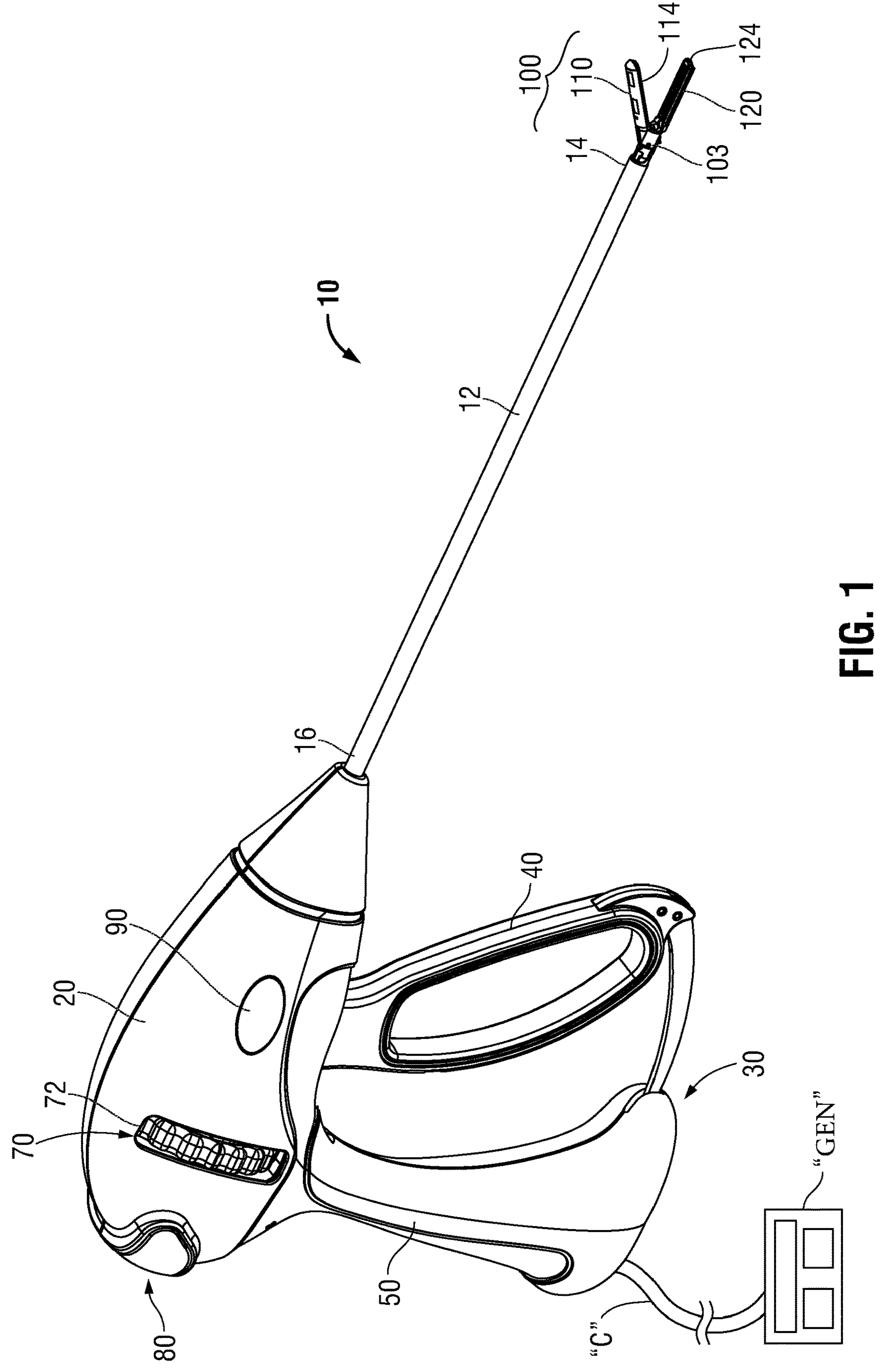
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "GEN." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 to provide energy thereto. First activation switch 80 is coupled to tissue-treating surfaces 114, 124 and the electrosurgical generator "GEN" for enabling the selective activation of the supply of energy, e.g., electrosurgical energy, to jaw members 110, 120 for treating, e.g., cauterizing, coagulating/desiccating, and/or sealing, tissue. Second activation switch 90 is coupled to a thermal cutting element (not shown) associated with end effector assembly 100 and the electrosurgical generator "GEN" (or a separate source of energy) for enabling the selective activation of the supply of energy, e.g., an AC signal, to the thermal cutting element for thermally cutting tissue. Various configurations of thermal cutting elements are detailed below with respect to the embodiments of FIGS. 4-13. Further, as an alternative to two separate activation switches 80, 90, a single activation switch (including one or more stages of activation) and/or more than two activation switches (each including one or more stages of activation) are also contemplated.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 2:
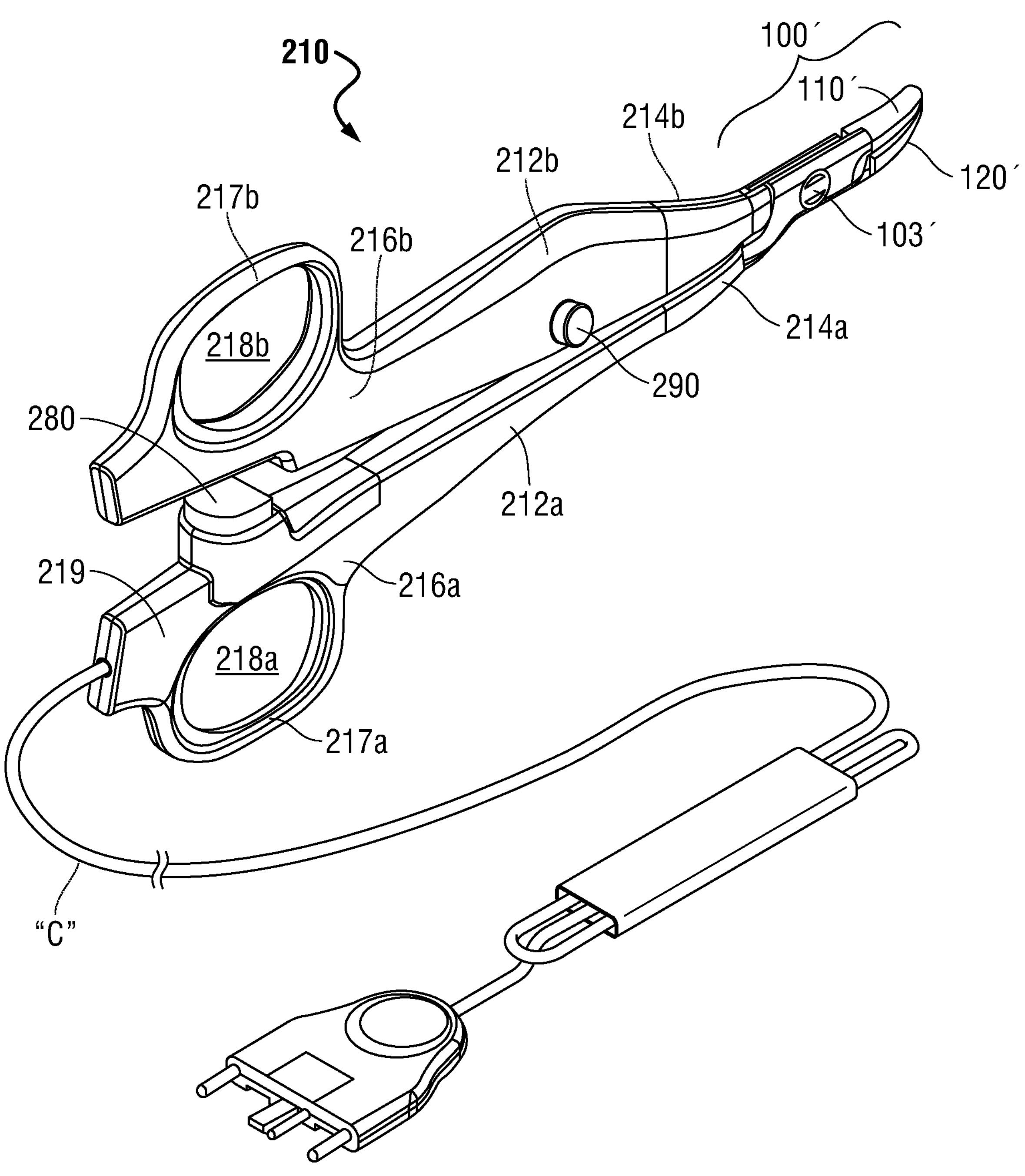
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Forceps 210 includes two elongated shaft members 212*a*, 212*b*, each having a proximal end portion 216*a*, 216*b*, and a distal end portion 214*a*, 214*b*, respectively. Forceps 210 is configured for use with an end effector assembly 100' similar to end effector assembly 100 (FIG. 1). More specifically, end effector assembly 100' includes first and second jaw members 110', 120' attached to respective distal end portions 214*a*, 214*b* of shaft members 212*a*, 212*b*. Jaw members 110', 120' are pivotably connected about a pivot 103'. Each shaft member 212*a*, 212*b* includes a handle 217*a*, 217*b* disposed at the proximal end portion 216*a*, 216*b* thereof. Each handle 217*a*, 217*b* defines a finger hole 218*a*, 218*b* therethrough for receiving a finger of the user. As can be appreciated, finger holes 218*a*, 218*b* facilitate movement of the shaft members 212*a*, 212*b* relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212*a*, 212*b* of forceps 210, e.g., shaft member 212*b*, includes a proximal shaft connector 219 configured to connect forceps 210 to a source of energy, e.g., electrosurgical generator "GEN" (FIG. 1). Proximal shaft connector 219 secures a cable "C" to forceps 210 such that the user may selectively supply energy to jaw members 110', 120' for treating tissue. More specifically, a first activation switch 280 is provided for supplying energy from electrosurgical generator "GEN" (FIG. 1) to jaw members 110', 120' to treat tissue upon sufficient approximation of shaft members 212*a*, 212*b*, e.g., upon activation of first activation switch 280 via shaft member 212*a*. A second activation switch 290 disposed on either or both of shaft members 212*a*, 212*b* is coupled to the thermal cutting element (not shown) of one of the jaw members 110', 120' of end effector assembly 100' and to the electrosurgical generator "GEN" (FIG. 1) for enabling the selective activation of the supply of energy to the thermal cutting element for thermally cutting tissue. Various configurations of thermal cutting elements are detailed below with respect to the embodiments of FIGS. 4-13. Similarly as detailed above with respect to forceps 10 (FIG. 1), as an alternative to two separate activation switches 280, 290, a single activation switch (including one or more stages of activation) and/or more than two activation switches (each including one or more stages of activation) are also contemplated.

Jaw members 110', 120' define a curved configuration wherein each jaw member is similarly curved laterally off of a longitudinal axis of end effector assembly 100'. However, other suitable curved configurations including curvature towards one of the jaw members 110', 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
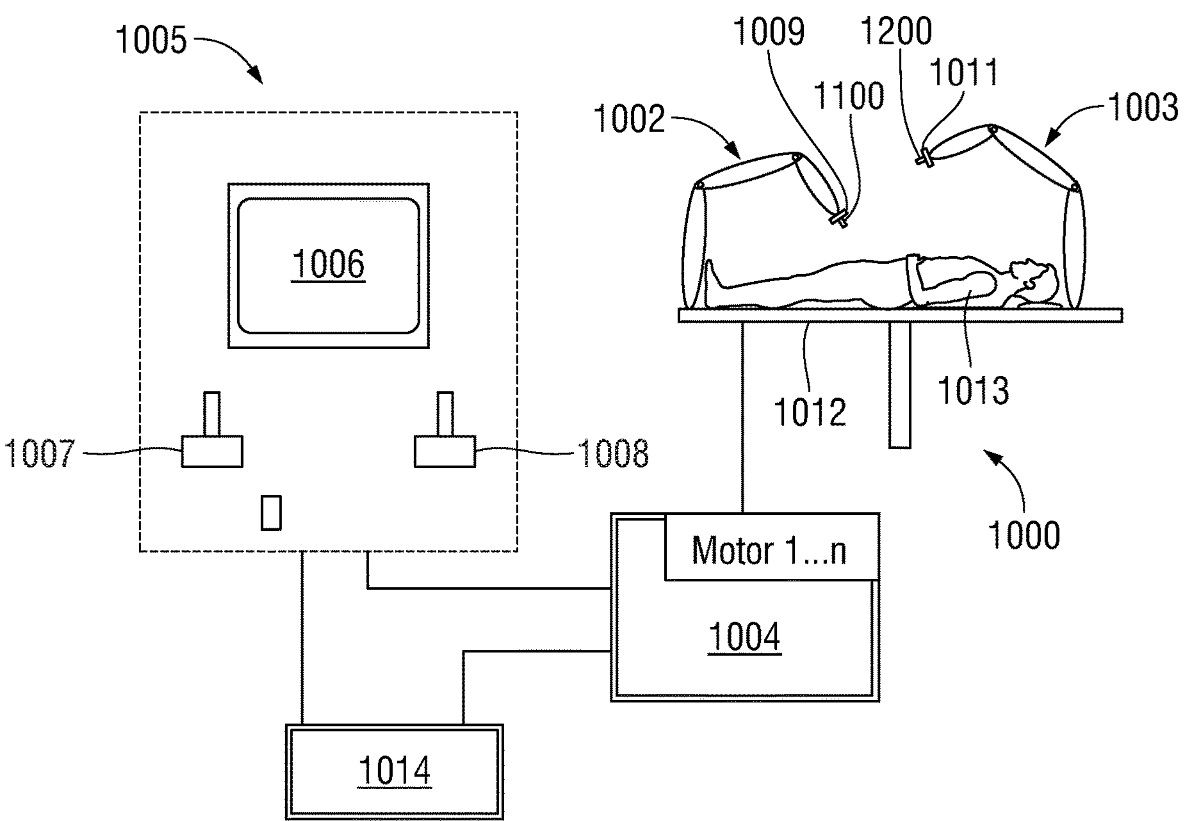
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIG. 1), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 4:
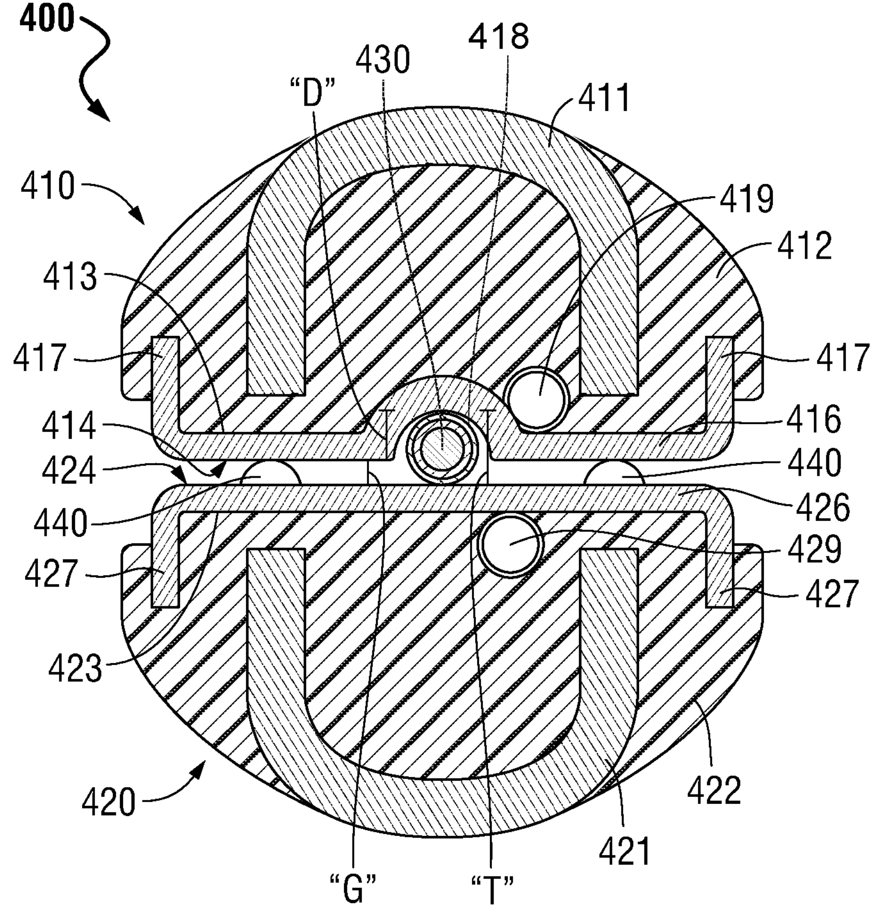
FIG. 4 is a transverse, cross-sectional view of jaw members of an end effector assembly provided in accordance with the present disclosure and configured for use with the surgical instruments of FIGS. 1-3 and/or any other suitable surgical instrument.

Turning to FIG. 4, an end effector assembly configured for use as end effector assembly 100 of forceps 10 (FIG. 1), end effector assembly 100' of forceps 210 (FIG. 2), end effector assembly 1100 of robotic surgical system 1000 (FIG. 3), or the end effector assembly of any other suitable surgical instrument is shown generally identified by reference numeral 400. End effector assembly 400 includes first and second jaw members 410, 420 each including a structural frame 411, 421, a jaw housing 412, 422, and a tissue-treating plate 413, 423 defining a respective tissue-treating surface 414, 424 thereof. One or both of jaw members 410, 420 is movable relative to the other from a spaced-apart position to an approximated position for grasping tissue between tissue-treating surfaces 414, 424 of tissue-treating plates 413, 423, respectively.

Structural frames 411, 421 provide structural rigidity to jaw members 410, 420 and extend proximally from jaw housings 412, 422 and tissue-treating plates 413, 423, respectively, to enable operable coupling of jaw members 410, 420 with one another as well as operable coupling of end effector assembly 400 with the distal end portion of a surgical instrument, e.g., distal end portion 14 of shaft 12 and the distal end portion of the drive assembly of forceps 10 (FIG. 1).

Jaw housings 412, 422 are formed from a thermally and electrically insulative material to electrically isolate structural frames 411, 421 from one or both of tissue-treating plates 413, 423. Jaw housings 412, 422 encapsulate at least a portion of structural frames 411, 421 therein and may be formed from one or more overmolds or in any other suitable manner. In embodiments, jaw housings 412, 422 also retain tissue-treating plates 413, 423, respectively, thereon, e.g., capturing legs 417, 427 of tissue-treating plates 413, 423, respectively, therein. One or more insulative spacers (not shown), may be incorporated into jaw housings 412 and/or 422, e.g., via overmolding.

Tissue-treating plates 413, 423, as noted above, define opposed tissue-treating surfaces 414, 424, respectively. Tissue-treating plates 413, 423, more specifically, define body portions 416, 426 having generally planar configurations that define tissue-treating surfaces 414, 424. Each tissue-treating plate 413, 423 further includes a leg 417, 427 extending from each side thereof. Legs 417, 427, as noted above, facilitate engagement of tissue-treating plates 413, 423 on jaw housings 412, 422. Electrical lead wires 419, 429 extend through jaw housings 412, 422 to electrically connect to the undersides of tissue-treating plates 413, 423, respectively, or are otherwise positioned, to enable the delivery of electrosurgical energy to tissue-treating plates 413, 423, e.g., for treating tissue grasped therebetween.

Continuing with reference to FIG. 4, at least one of the tissue-treating plates, e.g., tissue-treating plate 413, defines a longitudinally-extending depression 418 extending therealong. Depression 418 may define a rounded configuration e.g., having a semi-circular cross-sectional configuration, or any other suitable configuration. A thermal cutting element in the form of a thermal cutting wire 430 is disposed at least partially within depression 418 and extends longitudinally along at least a portion of tissue-treating surface 424. Depression 418 may define a diameter (or height and width, where depression is not semi-circular, that generally approximates, e.g., within 15% or other suitable percentage, the diameter "T" of thermal cutting wire 430 to complimentarily receive the at least a portion of thermal cutting wire 430 therein, although other configurations are also contemplated. Thermal cutting wire 430 may extend about the distal end of jaw member 410 and return proximally on the exterior thereof, may extend into jaw member 410 at a distal portion of jaw member 410, e.g., at or towards the distal end thereof, and return proximally through jaw member 410, or may define any other suitable configuration, such as those detailed hereinbelow. Depression 418 may retain thermal cutting wire 430 in position; additionally or alternatively, adhesives, other mechanical engagements, etc. may be used to retain thermal cutting wire in position at least partially within depression 418.

Thermal cutting wire 430 may be configured as a ferromagnetic thermal cutting wire including a solid conductive core and a ferromagnetic coating disposed about the solid conductive core. Thermal cutting wire 430 may further include an electrically-insulative coating surrounding at least a portion of the ferromagnetic coating to electrically isolate thermal cutting wire 430 from tissue-treating surfaces 414, 424. In embodiments, the solid conductive core is copper. In embodiments, the ferromagnetic coating is iron-nickel having a Curie temperature of between 400° C. and 600° C. and, in embodiments, of about 500° C. Other temperatures or temperature ranges are also contemplated. In embodiments, the electrically-insulative coating is a ceramic.

Thermal cutting wire 430, in embodiments where configured as a ferromagnetic thermal cutting wire, is configured for self-limiting temperature regulation to achieve and maintain a pre-determined temperature. More specifically, in the presence of a high-frequency alternating current, ferromagnetic materials generate large amounts of heat through the hysteresis of the magnetic field in the alternating current. Ferromagnetic materials also have a temperature where they cease to be ferromagnetic, referred to as the Curie temperature. Thus, once the material reaches the Curie temperature, the heating effect essentially ceases. That is, once the material ceases to be ferromagnetic, it becomes a much less effective heater thereby greatly decreasing its thermal output to the point where that temperature is maintained. Thus, the result is a heater that maintains a specific temperature based on its configuration and can be used to ensure sufficient heating and prevent overheating without the need for sensors, feedback mechanisms, and/or control loops. Further, in use, when the heated thermal cutting wire 430 contacts tissue and is cooled below the Curie temperature, e.g., by virtue of contact with the relatively cooler tissue, the ferromagnetic thermal cutting wire 430 again becomes ferromagnetic and once again becomes an effective heater to automatically heat back to the Curie temperature, thus providing self-regulation.

One or both of jaw members 410, 420 includes one or more stop members 440 associated with, e.g., disposed on, extending through, or otherwise positioned relative to, tissue-treating plates 413, 423 along at least a portion of the lengths thereof. The one or more stop members 440 extend beyond tissue-treating surfaces 414 and/or 424 towards the other tissue-treating surface 414, 424 to define a minimum gap distance "G" between jaw members 410, 420 at at least one position along the length thereof. This minimum gap distance "G" may be set based on contact between a stop member 440 and the opposing tissue-treating plate 413, 423, contact between opposing stop members 440, or in any other suitable manner. It is noted that this minimum gap distance "G" may correspond to the position of jaw members 410, 420 in the approximated position; alternatively, the approximated position may correspond to a position wherein tissue-treating surfaces 414, 424 are spaced-apart a distance greater than the minimum gap distance "G" in at least one location along the length thereof.

In embodiments, the minimum gap distance "G" plus the depth "D" of depression 418, e.g., the radius of depression 418 in embodiments where depression 418 is semi-circular, is equal to or greater than the diameter "T" of thermal cutting wire 430 to inhibit damage to thermal cutting wire 430, e.g., crushing of thermal cutting wire 430 from force applied by jaw members 410, 420.

In use, tissue is grasped between tissue-treating surfaces 414, 424 of jaw members 410, 420 and electrosurgical energy is supplied to tissue-treating plate 413, 423 for conduction through the grasped tissue to treat, e.g., seal, the grasped tissue, e.g., via activation of first activation switch 80 (FIG. 1). Thereafter, thermal cutting wire 430 is activated to thermally cut the treated tissue into to treated tissue portions e.g., via activation of second activation switch 90 (FIG. 1).

Figure 5:
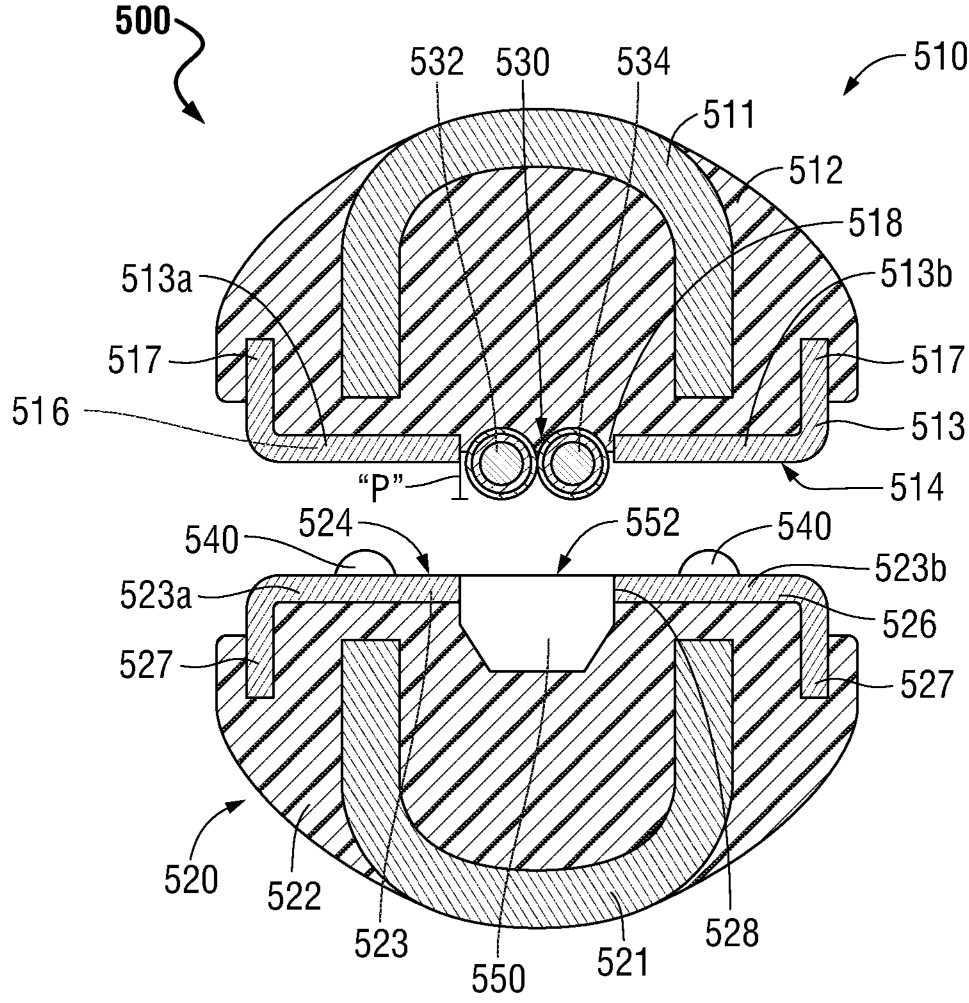
FIG. 5 is a transverse, cross-sectional view of jaw members of another end effector assembly provided in accordance with the present disclosure and configured for use with the surgical instruments of FIGS. 1-3 and/or any other suitable surgical instrument.

Turning to FIG. 5, another end effector assembly configured for use as end effector assembly 100 of forceps 10 (FIG. 1), end effector assembly 100' of forceps 210 (FIG. 2), end effector assembly 1100 of robotic surgical system 1000 (FIG. 3), or the end effector assembly of any other suitable surgical instrument is shown generally identified by reference numeral 500. End effector assembly 500 includes first and second jaw members 510, 520 each including a structural frame 511, 521, a jaw housing 512, 522, and a tissue-treating plate 513, 523 defining a respective tissue-treating surface 514, 524 thereof. One or both of jaw members 510, 520 is movable relative to the other from a spaced-apart position to an approximated position for grasping tissue between tissue-treating surfaces 514, 524 of tissue-treating plates 513, 523, respectively.

Structural frames 511, 521 provide structural rigidity to jaw members 510, 520 and extend proximally from jaw housings 512, 522 and tissue-treating plates 513, 523, respectively, to enable operable coupling of jaw members 510, 520 with one another as well as operable coupling of end effector assembly 500 with the distal end portion of a surgical instrument, e.g., distal end portion 14 of shaft 12 and the distal end portion of the drive assembly of forceps 10 (FIG. 1).

Jaw housings 512, 522 are formed from a thermally and electrically insulative material to electrically isolate structural frames 511, 521 from one or both of tissue-treating plates 513, 523. At least jaw housing 512 is formed from a high-temperature material, e.g., a material capable of withstanding temperatures of at least 400° C. Jaw housings 512, 522 encapsulate at least a portion of structural frames 511, 521 therein and may be formed from one or more overmolds or in any other suitable manner. In embodiments, jaw housings 512, 522 also retain tissue-treating plates 513, 523, respectively, thereon, e.g., capturing legs 517, 527 of tissue-treating plates 513, 523, respectively, therein. One or more insulative spacers (not shown), may be incorporated into jaw housings 512 and/or 522, e.g., via overmolding.

Tissue-treating plates 513, 523, as noted above, define opposed tissue-treating surfaces 514, 524, respectively. Tissue-treating plates 513, 523, more specifically, define body portions 516, 526 having generally planar configurations that define tissue-treating surfaces 514, 524. Each tissue-treating plate 513, 523 further includes a leg 517, 527 extending from each side thereof. Legs 517, 527, as noted above, facilitate engagement of tissue-treating plates 513, 523 on jaw housings 512, 522. Electrical lead wires (not shown) extend through jaw housings 512, 522 to electrically connect to the undersides of tissue-treating plates 513, 523, respectively, or are otherwise positioned, to enable the delivery of electrosurgical energy to tissue-treating plates 513, 523, e.g., for treating tissue grasped therebetween.

Continuing with reference to FIG. 5, the body 516, 526 of each tissue-treating plate 513, 523 defines a longitudinally-extending channel 518, 528 extending through at least a portion of the length thereof that divides the respective tissue-treating plate 513, 523 into first and second plate portions 513*a*, 513*b* and 523*a*, 523*b*, respectively. Channels 518, 528 may be laterally centered relative to jaw members 510, 520, respectively, or may be offset towards one side or the other and, thus, first and second plate portions 513*a*, 513*b* and 523*a*, 523*b*, respectively, may define equal or different widths. One of jaw members, e.g., jaw member 520, includes a high temperature elastomer 550, e.g., an elastomer capable of withstanding temperatures of at least 400° C., disposed within channel 528 and extending therealong. High-temperature elastomer 550 defines a tissue-contacting surface 552 that may be flush with, recessed relative to, or protruded from tissue-treating surface 524.

The other jaw member, e.g., jaw member 510, includes a thermal cutting element disposed partially within channel 518 and protruding therefrom. The thermal cutting element is in the form of a thermal cutting wire 530 including one or more wire segments. For example, thermal cutting wire 530 may include first and second wire segments 532, 534 disposed on the exposed portion of jaw housing 512 defined by channel 518 and extending in side-by-side relation relative to one another. Wire segments 532, 534 may be formed from a single wire that is bent at the distal end thereof, e.g., at a distal end portion of jaw member 510, such that first and second wire segments 532, 534 extend longitudinally along jaw member 510 at least partially within channel 518. Thermal cutting wire 530 is aligned with high-temperature elastomer 550 such that, in the approximated position of jaw members 510, 520, thermal cutting wire 530 is approximated relative to or contacts high-temperature elastomer 550.

Thermal cutting wire 530 may be a ferromagnetic thermal cutting wire configured similarly as detailed above with respect to thermal cutting wire 430 (FIG. 4) except that, since thermal cutting wire 530 is not in contact with tissue-treating surfaces 514, 524 and does not contact tissue-treating surfaces 514, 524 during use the electrically-insulative layer, e.g., ceramic, need not be provided (so long as sufficient electrical isolation is maintained between the various wires, tissue-treating surface, and/or any other electrical conduits).

One or both of jaw members 510, 520 includes one or more stop members 540 associated with, e.g., disposed on, extending through, or otherwise positioned relative to, tissue-treating plates 513, 523 along at least a portion of the lengths thereof. The one or more stop members 540 extend beyond tissue-treating surfaces 514 and/or 524 towards the other tissue-treating surface 514, 524 to define a minimum gap distance (not shown, similar to gap distance "G" (FIG. 4)) between jaw members 510, 520 at at least one position along the length thereof. This minimum gap distance may be set based on contact between a stop member 540 and the opposing tissue-treating plate 513, 523, contact between opposing stop members 540, or in any other suitable manner. It is noted that this minimum gap distance may correspond to the position of jaw members 510, 520 in the approximated position; alternatively, the approximated position may correspond to a position wherein tissue-treating surfaces 515, 525 are spaced-apart a distance greater than the minimum gap distance in at least one location along the length thereof.

In embodiments, the minimum gap distance is equal to or greater than the height "P" that wire segments 532, 534 of thermal cutting wire 530 protrude beyond tissue-treating surface 514 plus or minus any distance the tissue-contacting surface 552 of high temperature elastomer 550 protrudes or is recessed, respectively, relative to tissue-treating surface 524. Alternatively, the minimum gap distance may be less than the height "P" plus or minus any distance the tissue-contacting surface 552 of high temperature elastomer 550 protrudes or is recessed. In either configuration, in the approximated position of jaw members 510, 520, cutting wire 530 urges tissue grasped between jaw members 510, 520 into contact with high temperature elastomer 550 to at least partially elastically deform high temperature elastomer 550, although other non-deforming configurations are also contemplated.

In use, tissue is grasped between tissue-treating surfaces 514, 524 of jaw members 510, 520 and electrosurgical energy is supplied to tissue-treating plate 513, 523 for conduction through the grasped tissue to treat, e.g., seal, the grasped tissue. Thereafter, thermal cutting wire 530 is activated, thus activating wire segments 532, 534, to thermally cut the treated tissue into to treated tissue portions.

Figure 6A:
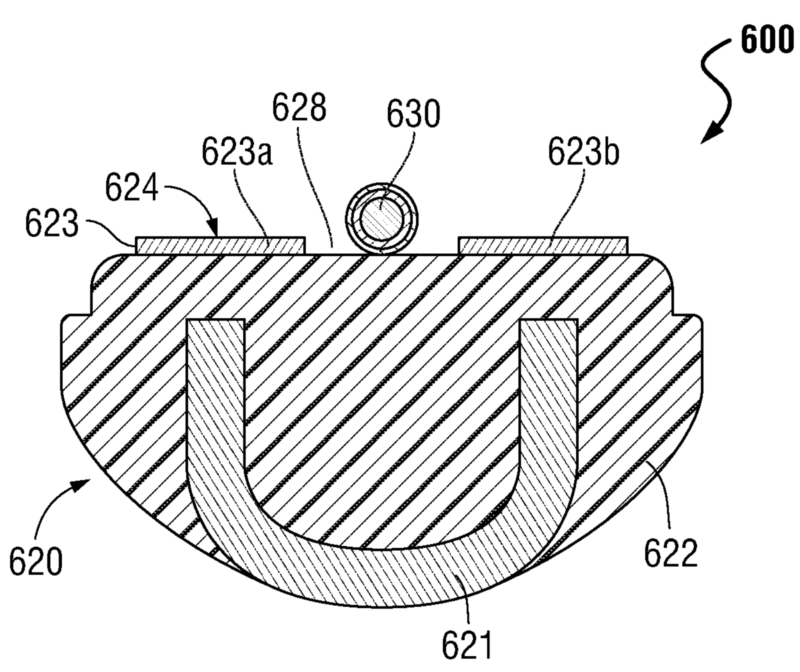
FIG. 6A is a transverse, cross-sectional view of a jaw member of still another end effector assembly provided in accordance with the present disclosure and configured for use with the surgical instruments of FIGS. 1-3 and/or any other suitable surgical instrument.

Turning to FIG. 6A, a jaw member 620 of another end effector assembly 600 is shown configured for use as end effector assembly 100 of forceps 10 (FIG. 1), end effector assembly 100' of forceps 210 (FIG. 2), end effector assembly 1100 of robotic surgical system 1000 (FIG. 3), or the end effector assembly of any other suitable surgical instrument. The other jaw member (not shown) of end effector assembly 600 may be similar to jaw member 620, jaw member 420 (FIG. 4), jaw member 520 (FIG. 5), combinations thereof, or may define any other suitable configuration. Further, jaw member 620 is similar to jaw member 410 (FIG. 4) and, thus, only the differences therebetween are described in detail below to avoid unnecessary repetition.

Jaw member 620 includes a structural frame 621, a jaw housing 622, and a tissue-treating plate 623 defining a tissue-treating surface 624 thereof. Jaw housing 622 is formed from a high-temperature electrically and thermally insulating material, e.g., a material capable of withstanding temperatures of at least 400° C. Tissue-treating plate 623 includes first and second plate portions 623*a*, 623*b* defining a channel 628 therebetween. Plate portions 623*a*, 623*b* may be joined with one another at distal end portions thereof or may remain spaced from one another. Plate portions 623*a*, 623*b* are formed via sputtering electrically-conductive material onto jaw housing 622 to form plate portions 623*a*, 623*b*. However, other suitable manufacturing techniques are also contemplated. One or more electrical lead wires, contacts, or other suitable connectors (not shown) disposed on or within jaw member 620 enable electrical connection to plate portions 623*a*, 623*b* to permit the delivery of electrosurgical energy thereto.

A thermal cutting element is disposed partially within channel 628 and protrudes therefrom. The thermal cutting element is in the form of a thermal cutting wire 630 including one or more wire segments (see, e.g., thermal cutting elements 430, 530 (FIGS. 4 and 5, respectively)). Thermal cutting wire 630 is disposed on the exposed portion of jaw housing 622 between plate portions 623*a*, 623*b*. Thermal cutting wire 630 may be a ferromagnetic thermal cutting wire configured similarly as detailed above with respect to thermal cutting wire 430 (FIG. 4) except that, since thermal cutting wire 630 is not in contact with plate portions 623*a*, 623*b* and does not contact plate portions 623*a*, 623*b*, or corresponding portions of the other jaw member, the electrically-insulative layer, e.g., ceramic, need not be provided.

Figure 6B:
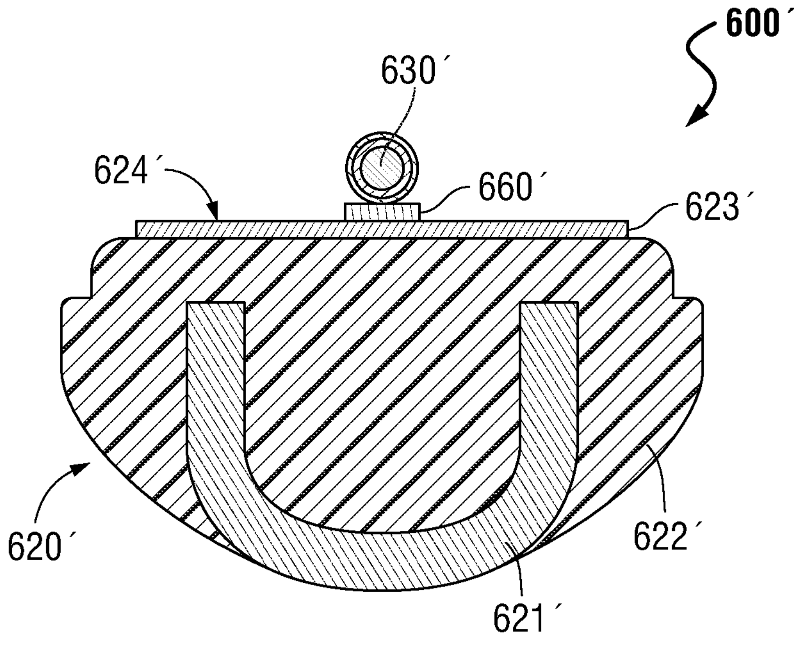
FIG. 6B is a transverse, cross-sectional view of a jaw member of yet another end effector assembly provided in accordance with the present disclosure and configured for use with the surgical instruments of FIGS. 1-3 and/or any other suitable surgical instrument.

Turning to FIG. 6B, a jaw member 620' of another end effector assembly 600' is shown configured for use as end effector assembly 100 of forceps 10 (FIG. 1), end effector assembly 100' of forceps 210 (FIG. 2), end effector assembly 1100 of robotic surgical system 1000 (FIG. 3), or the end effector assembly of any other suitable surgical instrument. The other jaw member (not shown) of end effector assembly 600' may be similar to jaw member 620', jaw member 420 (FIG. 4), jaw member 520 (FIG. 5), combinations thereof, or may define any other suitable configuration. Further, jaw member 620' is similar to jaw member 620 (FIG. 6A) and, thus, only the differences therebetween are described in detail below to avoid unnecessary repetition.

Jaw member 620' includes a structural frame 621', a jaw housing 622', and a tissue-treating plate 623' defining a tissue-treating surface 624' thereof. Tissue-treating plate 623' is formed as a single, continuous piece of material (in contrast to the first and second plate portions 623*a*, 623*b* of jaw member 620 (FIG. 6A)) via sputtering or other suitable manufacturing method.

Rather than defining a longitudinally-extending channel, jaw member 620' includes a longitudinally-extending electrical insulator 660' (or a series of longitudinally-spaced insulator portions) disposed on tissue-treating surface 624' of tissue-treating plate 623' and extending longitudinally along at least a portion of the length thereof. Electrical insulator 660' may be formed from a ceramic or other suitable material and may be sprayed onto tissue-treating surface 624', deposited onto tissue-treating surface 624', or disposed thereon in any other suitable manner. In such configurations, an electrically-insulative layer surrounding cutting wire 630' need not be provided.

Figure 12:
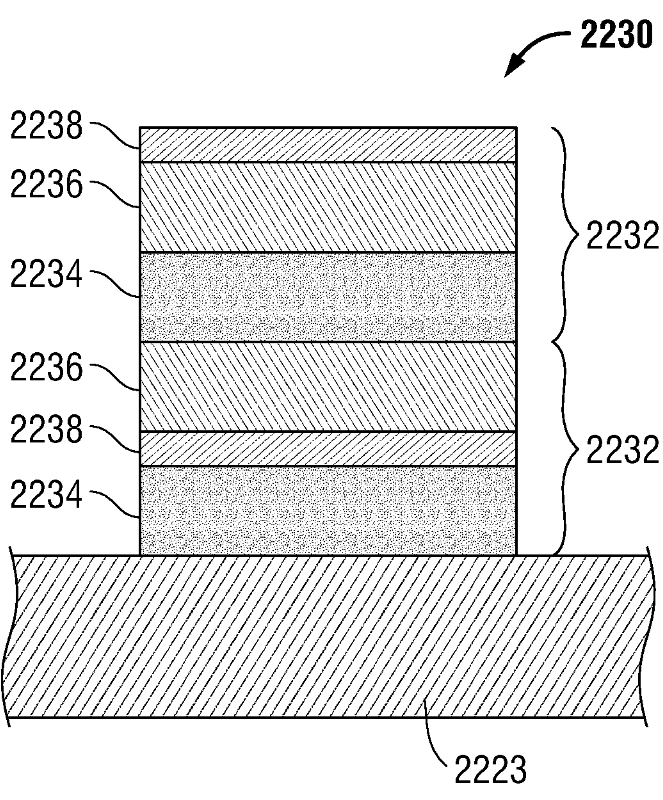
FIG. 12 is a transverse, cross-sectional view of a portion of a jaw member of another end effector assembly provided in accordance with the present disclosure and configured for use with the surgical instruments of FIGS. 1-3 and/or any other suitable surgical instrument.
Figure 13:
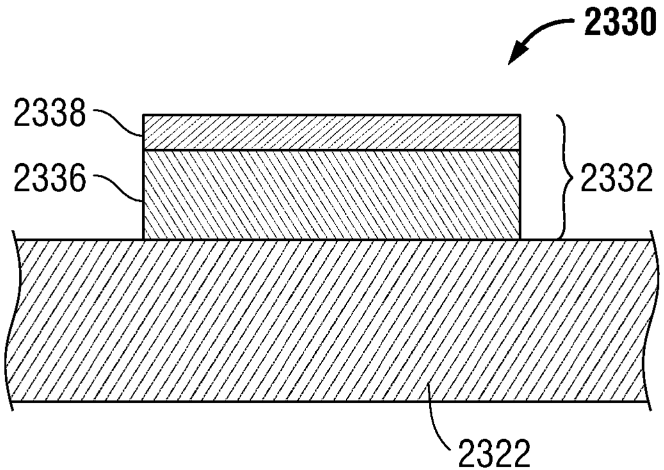
FIG. 13 is a transverse, cross-sectional view of a portion of a jaw member of yet another end effector assembly provided in accordance with the present disclosure and configured for use with the surgical instruments of FIGS. 1-3 and/or any other suitable surgical instrument.

A thermal cutting element is disposed on electrical insulator 660', electrically insulated from tissue-treating surface 624' thereby, and extends along at least a portion of the length of electrical insulator 660'. The thermal cutting element is in the form of a thermal cutting wire 630' including one or more wire segments (see, e.g., thermal cutting elements 430, 530 (FIGS. 4 and 5, respectively)). As an alternative to depositing electrical insulator 660' onto tissue-treating surface 624', electrical insulator 660' may be coated on at least a portion of thermal cutting wire 630' to provide an electrically-insulative coating on at least the portion of thermal cutting wire 630' that contacts tissue-treating surface 624' and/or the tissue-treating surface of the other jaw member. Thermal cutting wire 630' may be a ferromagnetic thermal cutting wire configured similarly as detailed above with respect to thermal cutting wire 430 (FIG. 4), or may be configured similar to thermal cutting elements 2230, 2330 (FIGS. 12 and 13, respectively).

Figure 7:
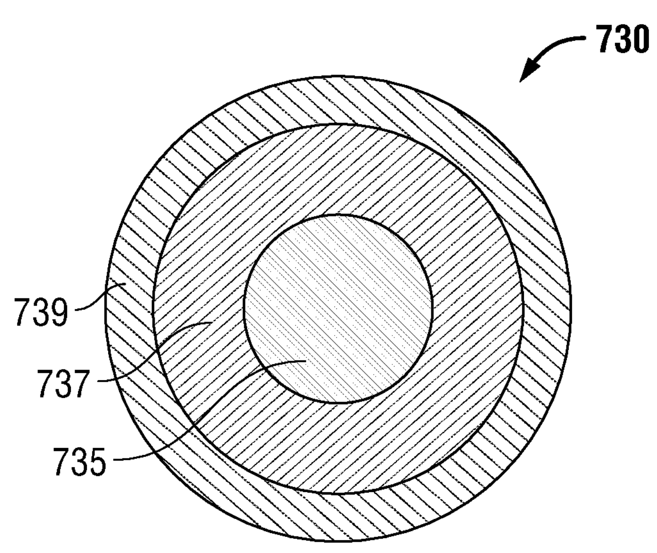
FIG. 7 is a transverse, cross-sectional view of a cutting wire provided in accordance with aspects of the present disclosure and configured for use with the surgical instruments of FIGS. 1-3 and/or any other suitable surgical instrument.

Referring to FIG. 7, another configuration of a ferromagnetic thermal cutting wire configured for use as thermal cutting wires 430 (FIG. 4), 530 (FIG. 5), 630 (FIG. 6A), and/or 630' (FIG. 6B) is shown generally identified by reference numeral 730. Ferromagnetic thermal cutting wire 730 includes a solid conductive core 735, e.g., copper, an inner ferromagnetic coating 737 disposed about the solid conductive core 735, and an outer ferromagnetic coating 739 disposed about the inner ferromagnetic coating 737. Inner and outer ferromagnetic coatings 737, 739 are formed from different materials and may define different thicknesses and/or overall volumes. In embodiments, inner ferromagnetic coating 737 defines a greater overall greater volume than outer ferromagnetic coating 739 and is formed from a relatively high magnetic loss material (as compared to outer ferromagnetic coating 739) while outer ferromagnetic coating 739 is formed from a material having a relatively higher permeability (as compared to inner ferromagnetic coating 737). As a result of this configuration, current is more concentrated and generates high ohmic loss within outer ferromagnetic coating 739 while the rest of the current within the relatively larger volume of the inner ferromagnetic coating 737 generates more magnetic loss, e.g., hysteresis loss.

Additionally or alternatively, inner and outer ferromagnetic coatings 737, 739 may be configured to define different Curie temperatures. More specifically, outer ferromagnetic coating 739 may define a Curie temperature that is less than the Curie temperature of inner ferromagnetic coating 737. As a result of this configuration, when the Curie temperature of the outer ferromagnetic coating 739 is first achieved, the output power does not immediately drop to zero (or close to zero); instead, the output power drops to a mid-point of power due to the fact that the inner ferromagnetic coating 737 maintains its magnetic properties and continues to be heated (via a lower output power) until it reaches its Curie temperature. The final temperature of thermal cutting wire 730 in such embodiments is between the Curie temperature of outer ferromagnetic coating 739 and the Curie temperature of inner ferromagnetic coating 737, while the transition of output power (from the relatively high power when both coatings 737, 739 are being heated to the relatively lower output power when only inner coating 737 is being heated) is relatively smooth.

Thermal cutting wire 730 may further include an electrically-insulative, e.g., ceramic, coating surrounding at least a portion of the outer ferromagnetic coating 739, similarly as detailed above.

Figure 8A:
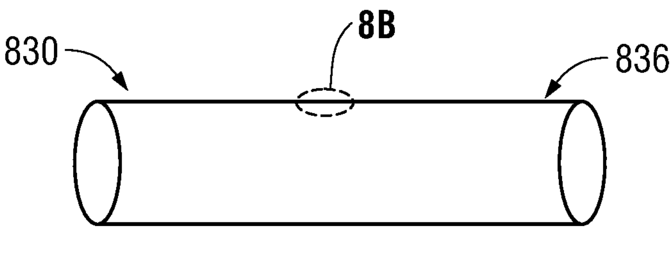
FIG. 8A is a side, perspective view of a portion of another cutting wire provided in accordance with aspects of the present disclosure and configured for use with the surgical instruments of FIGS. 1-3 and/or any other suitable surgical instrument.
Figure 8B:
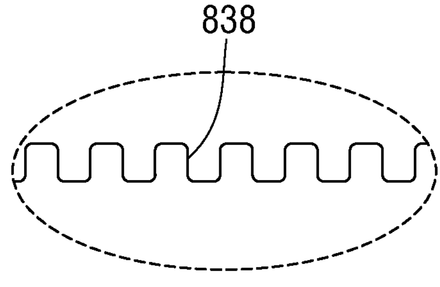
FIG. 8B is a greatly enlarged, side, perspective view of the area of detail indicated as "8B" in FIG. 8A.
Figure 9:
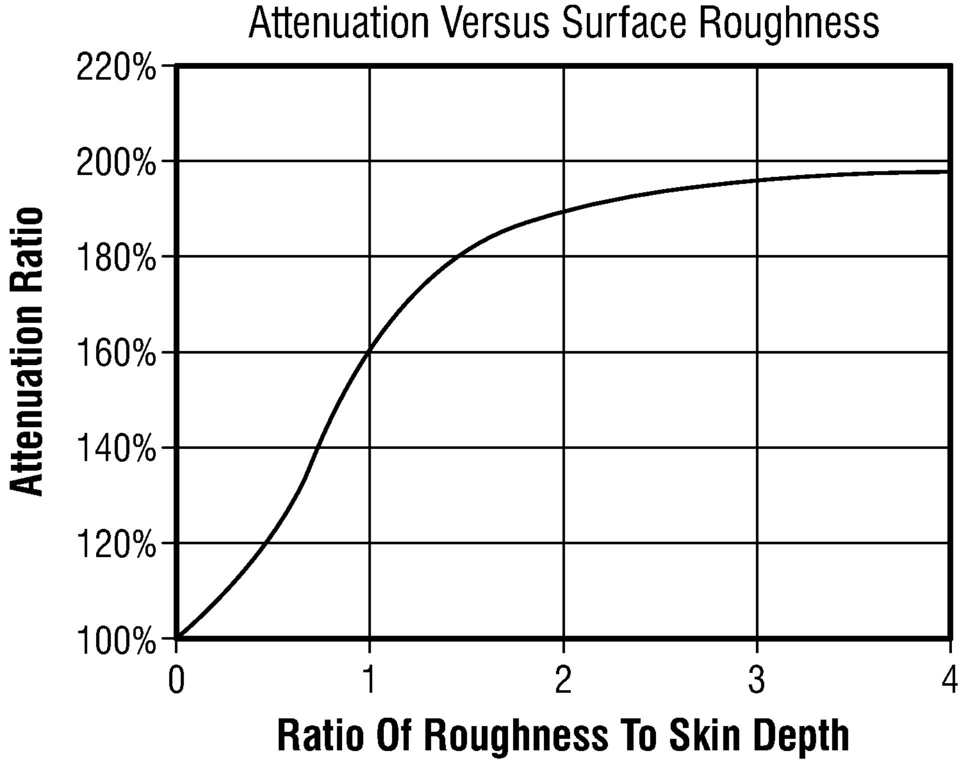
FIG. 9 is a graph illustrating attenuation versus surface roughness of a cutting wire provided in accordance with aspects of the present disclosure and configured for use with the surgical instruments of FIGS. 1-3 and/or any other suitable surgical instrument.

With reference to FIGS. 8A-9, another configuration of a ferromagnetic thermal cutting wire configured for use as thermal cutting wires 430 (FIG. 4), 530 (FIG. 5), 630 (FIG. 6A), 630' (FIG. 6B), and/or 730 (FIG. 7) is shown generally identified by reference numeral 830. Ferromagnetic thermal cutting wire 830 may be configured similar to any of the previous embodiments and/or include any of the features thereof in any suitable combination.

Referring to FIGS. 8A and 8B, ferromagnetic thermal cutting wire 830 further includes a surface roughness 838 defined on the outer peripheral surface 836 thereof. Due to the skin depth effect, current applied to a ferromagnetic material mostly concentrates on the surface layer (on the order of tens of microns) of the ferromagnetic material. As such, if a surface roughness 838 is introduced to increase the overall surface area of the surface layer, the current travel length as well as the average resistivity increases, effectively increasing AC resistance and heating efficiency.

It has been found that if the surface roughness 838, measured as the average peak-to-trough distance defined by the surface roughness 838 on the outer peripheral surface 836 of the ferromagnetic thermal cutting wire 830, is selected in accordance with the skin depth of the ferromagnetic thermal cutting wire 830, the output power of the ferromagnetic thermal cutting wire 830 may be significantly increased. Further, surface roughness 838 may also help heat dissipation from ferromagnetic thermal cutting wire 830 to tissue by enhancing the wire-tissue interface (contact area) for heat conduction. The surface roughness 838 may be formed by a surface treatment process such as etching (e.g., wet or dry plasma etching), a masked coating process, or other suitable process. The surface roughness 838 may be patterned or random.

Referring also to FIG. 9, as noted above, the output power of the ferromagnetic thermal cutting wire 830 may be significantly increased if the surface roughness 838 is selected in accordance with the skin depth of the ferromagnetic thermal cutting wire 830. The skin effect is the tendency of an alternating electric current (AC) to become distributed within a conductor such that the current density is largest near the surface of the conductor, and decreases with greater depths in the conductor. The electric current flows mainly at this “skin” of the conductor, from the outer surface down to a level called the skin depth. The skin effect causes the effective resistance of the conductor to increase at higher frequencies where the skin depth is smaller, thus reducing the effective cross-section of the conductor. Thus, by configuring ferromagnetic thermal cutting wire 830 to correlate the surface roughness 838 with the skin depth according to a surface roughness to skin depth ratio, increased attenuation (loss) can be achieved. For example, as illustrated in FIG. 9, a study has shown that where the surface roughness is 2-3 times the skin depth, a ratio of between 2:1 and 3:1, the attenuation (loss) is increased to almost 200% as compared to a non-roughened cutting wire. At ratios above 3:1, further increase of attenuation (loss) tapers off to a negligible amount. Accordingly, in embodiments, the ferromagnetic thermal cutting wire 830 may define a surface roughness to skin depth ratio of from 2:1 to 3:1, although other ratios are also contemplated.

Figures 10A, 10B:
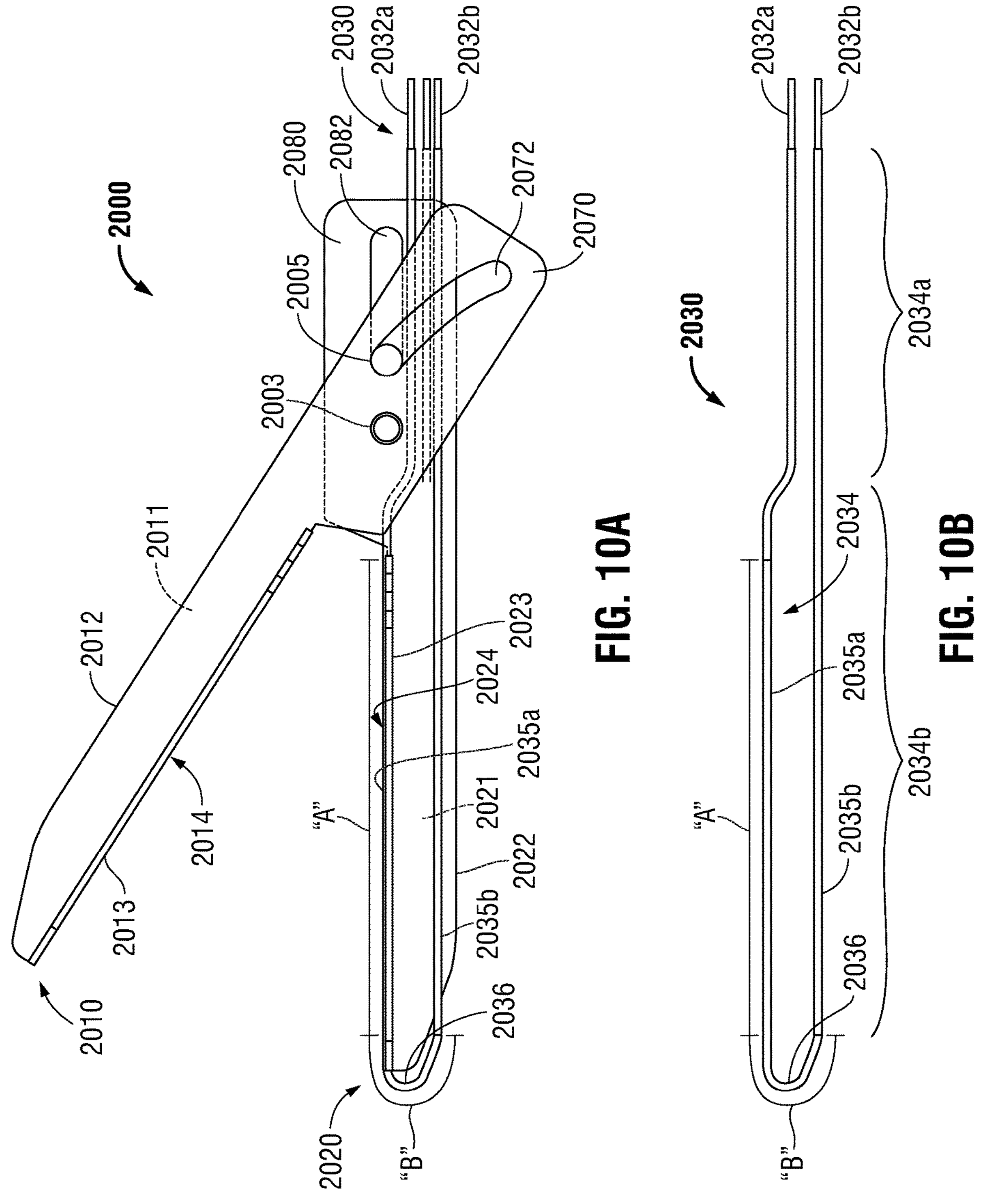
FIG. 10A is a longitudinal, cross-sectional view of yet another end effector assembly provided in accordance with the present disclosure and configured for use with the surgical instruments of FIGS. 1-3 and/or any other suitable surgical instrument.
FIG. 10B is a side, perspective view of a cutting wire of the end effector assembly of FIG. 10A.

FIG. 10A illustrates another end effector assembly configured for use as end effector assembly 100 of forceps 10 (FIG. 1), end effector assembly 100' of forceps 200 (FIG. 2), end effector assembly 1100 of robotic surgical system 1000 (FIG. 3), or the end effector assembly of any other suitable surgical instrument is shown generally identified by reference numeral 2000. End effector assembly 2000 may be configured similar to any of the end effector assemblies detailed hereinabove, except as explicitly contradicted below. Accordingly, only the different features of end effector assembly 2000 as detailed below while similarities are summarily described or omitted entirely.

End effector assembly 2000 includes first and second jaw members 2010, 2020 each including a structural frame 2011, 2021, a jaw housing 2012, 2022, and a tissue-treating plate 2013, 2023 defining a respective tissue-treating surface 2014, 2024 thereof. One or both of jaw members 2010, 2020 is movable relative to the other from a spaced-apart position to an approximated position for grasping tissue between tissue-treating surfaces 2014, 2024 of tissue-treating plates 2013, 2023, respectively. More specifically, structural frames 2011, 2021 extend proximally from jaw housings 2012, 2022 to define proximal flange portions 2070, 2080 enabling pivotable coupling of jaw members 2010, 2020 to one another and the distal end portion of a surgical instrument, e.g., distal end portion 14 of shaft 12 of forceps 10 (FIG. 1), about a pivot pin 2003. Proximal flange portions 2070, 2080 further define cam slots 2072, 2082, respectively, for receipt of a cam pin 2005 to operably couple jaw members 2010, 2020 with one another and a drive assembly such that actuation of the drive assembly pivots at least one of jaw members 2010, 2020 relative to the other between the spaced-apart and approximated positions.

With additional reference to FIG. 10B, end effector assembly 2000 further includes a thermal cutting element in the form of a thermal cutting wire 2030. Thermal cutting wire 2030 defines a loop configuration including first and second ends 2032*a*, 2032*b*, a body 2034 having first and second wire segments 2035*a*, 2035*b* and including a proximal body portion 2034*a* and a distal body portion 2034*b*, and a distal connector portion 2036 connecting the first and second wire segments 2035*a*, 2035*b* with one another. The above-detailed segments and portions are provide for identification purposes only and need not be separate pieces; rather, it is contemplated that thermal cutting wire 2030 be formed as a continuous, single strand of wire.

First and second ends 2032*a*, 2032*b* of thermal cutting wire 2030 both extend proximally from end effector assembly 2000, e.g., through shaft 12, housing 20, and cable "C" of forceps 10, to connect to an energy source, e.g., electrosurgical generator "GEN" (see FIG. 1). Proximal body portion 2034*a* of thermal cutting wire 2030 extends along proximal flange portion 2080 of jaw member 2020 below cam pin 2005 and pivot pin 2003. In embodiments, proximal flange portion 2080 defines a bifurcated configuration including first and second spaced-apart proximal flange components; in such embodiments, proximal body portion 2034*a* of thermal cutting wire 2030 may extend between the proximal flange components. First and second wire segments 2035*a*, 2035*b* are disposed a first distance apart from one another along proximal body portion 2034*a*.

First and second wire segments 2035*a*, 2035*b*, along distal body portion 2034*b* of thermal cutting wire 2030, are disposed a second, greater distance apart from one another. First wire segment 2035 extends on top, alongside, within a channel or depression, or otherwise along the tissue-contacting surface 2024 defined by tissue-treating plate 2023 of jaw member 2020, e.g., similarly as any of the embodiments detailed hereinabove or in any other suitable configuration, while second wire segment 2035*b* extends within jaw housing 2022. In other embodiments, second wire segment 2035*b* extends along an outer exterior surface of jaw housing 2022, or extends partially within jaw housing 2022 and partially along the outer exterior surface thereof. The portion of first wire segment 2035*a* extending along distal body portion 2034*b* of thermal cutting wire 2030 functions as a cutting wire to cut tissue grasped between jaw members 2010, 2020, e.g., to thermally cut sealed tissue, similarly as detailed above with respect to previous embodiments.

Distal connector portion 2036 of thermal cutting wire 2030 extends about at least a portion of the distal tip of jaw member 2020, e.g., distally about the distal tip of jaw housing 2022, to interconnect the distal ends of first and second wire segments 2035*a*, 2035*b* with one another. As such, distal connector portion 2036 is exposed at the distal tip of jaw member 2020 and functions as a cutting wire to cut tissue distally adjacent jaw member 2020, e.g., for thermal blunt dissection.

Thermal cutting wire 2030 may be configured as a ferromagnetic cutting wire. However, only the portion of first wire segment 2035*a* extending along distal body portion 2034*b* of thermal cutting wire 2030 and distal connector portion 2036 of thermal cutting wire 2030 are ferromagnetic, e.g., include a ferromagnetic coating, such that only these portions are heated when an alternating current (AC signal) is applied to thermal cutting wire 2030. The remainder of thermal cutting wire 2030 may be coated with a thermally and/or electrically insulative material.

In embodiments, the portion of first wire segment 2035*a* extending along distal body portion 2034*b* of thermal cutting wire 2030, defining a zone "A," has a first Curie temperature while distal connector portion 2036 of thermal cutting wire 2030, defining a zone "B," has a second, different Curie temperature. The different Curie temperatures may be achieved by the use of different ferromagnetic coatings, different layers (types, numbers, etc.) of ferromagnetic coating, different thicknesses, or in any other suitable matter. In other embodiments, the portion of first wire segment 2035*a* extending along distal body portion 2034*b* of thermal cutting wire 2030 and distal connector portion 2036 of thermal cutting wire 2030 define the same configuration and the same Curie temperature. The portion of first wire segment 2035*a* extending along distal body portion 2034*b* of thermal cutting wire 2030 and distal connector portion 2036 of thermal cutting wire 2030 may be configured similarly or differently and may each include any or all of the features detailed above with respect to ferromagnetic thermal cutting wire 830 (FIGS. 8A and 8B) or may define any other suitable configuration. The portion of first wire segment 2035*a* extending along distal body portion 2034*b* of thermal cutting wire 2030 and distal connector portion 2036 of thermal cutting wire 2030 may be coated with an electrically electrically non-conductive material, e.g., ceramic, to electrically isolate the same from tissue-treating plates 2013, 2023.

Figures 11A, 11B:
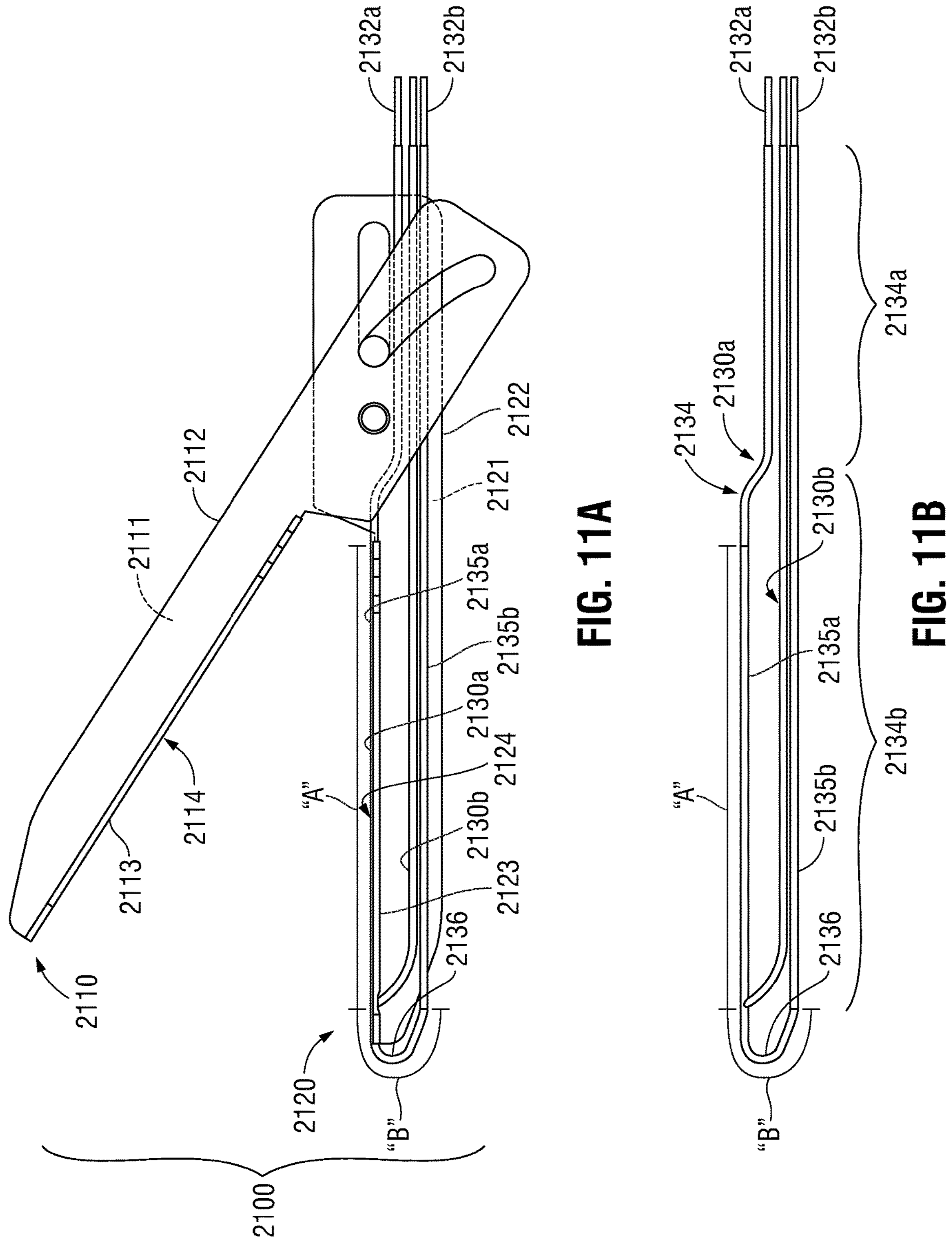
FIG. 11A is a longitudinal, cross-sectional view of still yet another end effector assembly provided in accordance with the present disclosure and configured for use with the surgical instruments of FIGS. 1-3 and/or any other suitable surgical instrument.
FIG. 11B is a side, perspective view of cutting wires of the end effector assembly of FIG. 11A.

Turning to FIG. 11A, yet another end effector assembly configured for use as end effector assembly 100 of forceps 10 (FIG. 1), end effector assembly 100' of forceps 210 (FIG. 2), end effector assembly 1100 of robotic surgical system 1000 (FIG. 3), or the end effector assembly of any other suitable surgical instrument is shown generally identified by reference numeral 2100. End effector assembly 2100 is similar to end effector assembly 2000 (FIG. 10A) and may include any of the features thereof, except as explicitly contradicted below. Accordingly, only the different features of end effector assembly 2100 as detailed below while similarities are summarily described or omitted entirely.

End effector assembly 2100 includes first and second jaw members 2110, 2120 each including a structural frame 2111, 2121, a jaw housing 2112, 2122, and a tissue-treating plate 2113, 2123 defining a respective tissue-treating surface 2114, 2124 thereof. One or both of jaw members 2110, 2120 is movable relative to the other from a spaced-apart position to an approximated position for grasping tissue between tissue-treating surfaces 2114, 2124 of tissue-treating plates 2113, 2123, respectively.

With additional reference to FIG. 11B, end effector assembly 2100 further includes a thermal cutting assembly including first and second wires 2130*a*, 2130*b*. First wire 2130*a* is configured similar to and may include any of the features of thermal cutting wire 2030 (FIGS. 10A and 10B). That is, first wire 2130*a* defines a loop configuration including first and second ends 2132*a*, 2132*b*, a body 2134 having first and second wire segments 2135*a*, 2135*b* and including a proximal body portion 2134*a* and a distal body portion 2134*b*, and a distal connector portion 2136 connecting the first and second wire segments 2135*a*, 2135*b* with one another.

First wire 2130*a* may be configured as a ferromagnetic cutting wire wherein the portion of first wire segment 2135*a* extending along distal body portion 2134*b* of first wire 2130*a*, defining zone "A," and distal connector portion 2136 of first wire 2130*a*, defining zone "B," are ferromagnetic, e.g., include a ferromagnetic coating, such that only these portions are heated when an alternating current (AC signal) is applied to thermal cutting wire 2030. The remainder of first wire 2130*a* may be coated with a thermally and/or electrically insulative material.

Second wire 2130*b* branches off from first wire 2130*a* between first wire segment 2135*a* and distal connector portion 2136. Second wire 2130*b*, more specifically, extends from first wire 2130*a* through an opening defined within tissue-treating plate 2123 and/or jaw housing 2122 into or through jaw housing 2122 and returns proximally within jaw housing 2122, along an outer exterior surface of jaw housing 2122, or partially within jaw housing 2122 and partially along the outer exterior surface thereof, eventually extending proximally from end effector assembly 2100, e.g., through shaft 12, housing 20, and cable "C" of forceps 10, to connect to an energy source, e.g., electrosurgical generator "GEN" (see FIG. 1). Second wire 2130*b* may be coated with a thermally and/or electrically insulative material.

As a result of the above-detailed configuration, wherein the proximal end of second wire 2130*b* as well as the first and second ends 2132*a*, 2132*b* of first wire 2130*a* are connected to the energy source e.g., electrosurgical generator "GEN" (see FIG. 1), an alternating current (AC signal) can be supplied to selectively energize zone "A" and/or zone "B." Further, zone "A" and zone "B" may define similar or different Curie temperatures, e.g., via use of different ferromagnetic coatings, different layers of ferromagnetic coating, different thicknesses, or in any other suitable matter, and/or may be configured similarly or differently including any or all of the features detailed above with respect to ferromagnetic thermal cutting wire 830 (FIGS. 8A and 8B) or may define any other suitable configuration. Zone "A" and/or zone "B" may also include a ceramic or other suitable electrically-insulative coating, e.g., to electrically isolate the same from tissue-treating plates 2113, 2123.

In embodiments, rather than first wire 2130*a* defining zone "A" and zone "B" and second wire 2130*b* branching from first wire 2130*a*, first and second wires 2130*a*, 2130*b* may be separate from one another with each defining one of zone "A" and zone "B" and each including first and second ends that extend proximally to connect to an energy source, e.g., electrosurgical generator "GEN" (see FIG. 1). Other configurations are also contemplated.

With reference to FIG. 12, as an alternative to or in addition to providing one or more thermal cutting wires, one or both of the jaw members of any of the end effector assemblies detailed herein above, or may other suitable end effector assembly, may include a thermal cutting element 2230 disposed on the tissue-treating plate 2223 thereof. Thermal cutting element 2230 includes one or more sets of layers 2232 with each set of layers 2232 including: an electrical insulation layer 2234, e.g., ceramic; a conductive core layer 2236, e.g., copper; and a ferromagnetic layer 2238, e.g., iron-nickel. With respect to the first set of layers 2232, electrical insulation layer 2234 is disposed on tissue-treating plate 2223 to electrically isolate thermal cutting element 2230 from tissue-treating plate 2223, ferromagnetic layer 2238 is disposed on insulation layer 2234, and conductive core layer 2236 is disposed on ferromagnetic layer 2238 and connects to a source of energy to enable current flow through thermal cutting element 2230 while ferromagnetic layer 2238 enables ferromagnetic heating with automatic Curie temperature control upon the flow of current through conductive core layer 2236.

With respect to the second set of layers 2232, electrical insulation layer 2234 is disposed on the conductive core layer 2236 of the first set of layers 2232 to electrically isolate the first and second layers from one another, conductive core layer 2236 is disposed on electrical insulation layer 2234 and connects to a source of energy to enable current flow through thermal cutting element 2230, and ferromagnetic layer 2238 is disposed on conductive core layer 2236 and enables ferromagnetic heating with automatic Curie temperature control upon the flow of current through conductive core layer 2236.

In embodiments, multiple ferromagnetic layers 2238 may be stacked on top of one another and/or the exposed surface of the ferromagnetic layer(s) 2238 may be roughened, similarly as detailed above. Further, additional sets of layers 2232 similar as the first set of layers 2232 may be stacked on top of one another with the second set of layers 2232 disposed on the upper-most set of layers 2238. Alternatively, only a single set of layers 2232 may be provided, e.g., similar as the second set of layers 2232.

Referring to FIG. 13, as an alternative to or in addition to providing one or more thermal cutting wires, one or both of the jaw members of any of the end effector assemblies detailed herein above, or may other suitable end effector assembly, may include a thermal cutting element 2330 disposed on an exposed surface of the jaw housing 2322 thereof (where jaw housing 2322 is formed from a high-temperature electrically and thermally insulating material, e.g., a material capable of withstanding temperatures of at least 400° C.). The exposed surface of the jaw housing 2322 may be an exposed surface defined by a channel within the tissue-treating plate of the jaw member, an exposed surface defined between tissue-treating plate portions of the jaw member; an outer exterior, e.g., side or back surface, of the jaw housing 2322, or any other suitable exposed surface of jaw housing 2322.

Thermal cutting element 2330 includes one or more sets of layers 2332 with each set of layers 2332 including a conductive core layer 2336, e.g., copper; and a ferromagnetic layer 2338, e.g., iron-nickel. Conductive core layer 2336 is disposed on jaw housing 2322 and connects to a source of energy to enable current flow through thermal cutting element 2330 while ferromagnetic layer 2338 is disposed on conductive core layer 2336 and enables ferromagnetic heating with automatic Curie temperature control upon the flow of current through conductive core layer 2336. In embodiments, multiple ferromagnetic layers 2338 may be stacked on top of one another and/or the exposed surface of the ferromagnetic layer(s) 2338 may be roughened, similarly as detailed above. Further, additional sets of layers 2332 similarly arranged may be disposed on the first set of layers 2332 with an insulation layer, e.g., ceramic, disposed therebetween to provide electrical isolation.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:

an end effector assembly, including:

a first jaw member and a second jaw member, at least one of the first jaw member or the second jaw member movable relative to the other from a spaced-apart position to an approximated position to grasp tissue between a first opposed tissue-treating surface and a second opposed tissue-treating surface of the first jaw member and the second jaw member, the first jaw member including:

a first thermal cutting wire portion defining a first end and extending distally along at least a portion of a length of the first opposed tissue-treating surface;

a second thermal cutting wire portion extending about a distal tip of the first jaw member and defining a second end, the first thermal cutting wire portion and the second thermal cutting wire portion each including a ferromagnetic coating, wherein an exposed outer surface of the ferromagnetic coating has a roughness configured to facilitate attenuation during ferromagnetic heating, the roughness measured as an average peak-to-trough distance, wherein a ratio of the roughness to a skin depth of at least one of the first thermal cutting wire portion or the second thermal cutting wire portion is at least 1:3; and a third thermal cutting wire portion defining a third end, being electrically connected to the first thermal cutting wire portion and the second thermal cutting wire portion, and branching off from the first thermal cutting wire portion and the second thermal cutting wire portion, the third thermal cutting wire portion extending through an interior of the first jaw member;

wherein each of the first end, the second end, and the third end is adapted to connect to an energy source, enabling the first and second thermal cutting wire portions to be independently activatable allowing automatic Curie temperature control to each respective portion upon supply of an AC signal thereto.

2. The electrosurgical instrument according to claim 1, wherein the roughness is patterned.

3. The electrosurgical instrument according to claim 1, wherein the roughness is random.

4. The electrosurgical instrument according to claim 1, wherein the ratio of the roughness to the skin depth is between 2:1 and 3:1.

5. The electrosurgical instrument according to claim 1, wherein the ratio of the roughness to the skin depth is at least 2:1.

6. The electrosurgical instrument according to claim 1, wherein the ratio of the roughness to the skin depth is at least 1:1.

7. The electrosurgical instrument according to claim 1, wherein each of the first thermal cutting wire portion and the second thermal cutting wire portion includes a conductive core, an inner ferromagnetic coating disposed about the conductive core, and an outer ferromagnetic coating disposed about the inner ferromagnetic coating, and wherein the inner ferromagnetic coating defines a first thickness and the outer ferromagnetic coating defines a second, different thickness.

8. The electrosurgical instrument according to claim 7, wherein the first thickness is greater than the second thickness.

9. The electrosurgical instrument according to claim 7, wherein the inner ferromagnetic coating is formed from a first material and the outer ferromagnetic coating is formed from a second, different material.

10. The electrosurgical instrument according to claim 9, wherein the second material defines a relatively greater permeability compared to the first material.

11. The electrosurgical instrument according to claim 9, wherein the first material defines a relatively greater magnetic loss compared to the second material.

12. The electrosurgical instrument according to claim 7, wherein the inner ferromagnetic coating defines a first Curie temperature and the outer ferromagnetic coating defines a second Curie temperature different from the first Curie temperature.

13. The electrosurgical instrument according to claim 12, wherein the second Curie temperature is greater than the first Curie temperature.

* * * * *